United States Patent [19]

Ptchelintsev et al.

[11] Patent Number: 6,071,962

[45] Date of Patent: *Jun. 6, 2000

[54] OXA ACIDS AND RELATED COMPOUNDS FOR TREATING SKIN CONDITIONS

[75] Inventors: Dmitri Ptchelintsev, Mahwah; Neil D. Scancarella, Wyckoff; Robert Kalafsky, Ogdensburg, all of N.J.

[73] Assignee: Avon Products, Inc., New York, N.Y.

[ * ] Notice: This patent is subject to a terminal disclaimer.

[21] Appl. No.: 09/152,574

[22] Filed: Sep. 14, 1998

Related U.S. Application Data

[62] Division of application No. 08/658,089, Jun. 4, 1996, Pat. No. 5,847,003.

[51] Int. Cl.[7] .................. A61K 31/19; A61K 31/255; A61K 31/265
[52] U.S. Cl. .................. 514/558; 514/513; 514/559; 514/560
[58] Field of Search .................... 514/513, 558, 514/559, 560

[56] References Cited

U.S. PATENT DOCUMENTS

| | | | |
|---|---|---|---|
| 3,342,858 | 9/1967 | Fuhrman et al. | 260/531 |
| 4,136,098 | 1/1979 | Burzin et al. | 260/343 |
| 4,153,726 | 5/1979 | Borggrefe et al. | 424/313 |
| 4,254,105 | 3/1981 | Fukuda | 424/170 |
| 4,292,326 | 9/1981 | Nazzaro-Porro | 424/317 |
| 4,386,104 | 5/1983 | Nazzaro-Porro | 424/317 |
| 4,721,579 | 1/1988 | Kim | 252/79 |
| 4,766,153 | 8/1988 | Casciani | 514/785 |
| 4,885,282 | 12/1989 | Thornfeldt | 514/53 |
| 4,916,206 | 4/1990 | Day et al. | 528/272 |
| 4,960,764 | 10/1990 | Figueroa, Jr. et al. | 514/63 |
| 5,008,443 | 4/1991 | Day et al. | 560/169 |
| 5,017,675 | 5/1991 | Marten et al. | 528/111 |
| 5,087,440 | 2/1992 | Cacheris et al. | 424/9 |
| 5,091,171 | 2/1992 | Yu et al. | 424/642 |
| 5,098,692 | 3/1992 | Gries et al. | 424/9 |
| 5,108,751 | 4/1992 | Hagan et al. | 424/401 |
| 5,282,987 | 2/1994 | Balzer et al. | 252/34 |
| 5,319,004 | 6/1994 | Marten et al. | 523/404 |
| 5,385,943 | 1/1995 | Nazzaro-Porro | 514/574 |
| 5,464,929 | 11/1995 | Bezwada et al. | 528/361 |
| 5,639,897 | 6/1997 | O'Lenick, Jr. | 554/59 |
| 5,730,991 | 3/1998 | Rapaport | 424/401 |
| B1 5,091,171 | 9/1995 | Yu et al. | 424/642 |
| B2 5,091,171 | 7/1997 | Yu et al. | 424/642 |

FOREIGN PATENT DOCUMENTS

| | | |
|---|---|---|
| 2936123 | 9/1979 | Germany . |
| 3109498 | 5/1991 | Japan . |
| 7316587 | 12/1995 | Japan . |

OTHER PUBLICATIONS

Okamoto, K. Yukagaku, (1974), 23(11), p. 726–9 (Abstract HCAPLUS 1975:133667).

*Primary Examiner*—Phyllis G. Spivack
*Attorney, Agent, or Firm*—Ohlandt, Greeley, Ruggiero & Perle, LLP

[57] ABSTRACT

Disclosed the use of compounds of Formula (I) depicted below, as active principals for treating skin conditions, compositions containing these compounds, and methods of treating skin conditions using these compounds and compositions.

(I)

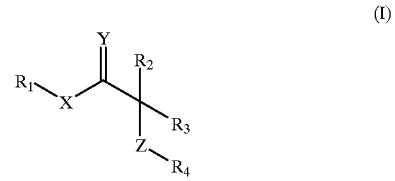

where $R_4$ is $(CR_5R_6-CR_7R_8-X_1)_n-CR_9R_{10}R_{11}$; n is an integer from 1 to 18; $R_1$, $R_2$, $R_3$, $R_5$, $R_6$, $R_7$, $R_8$, $R_9$, $R_{10}$ and $R_{11}$ are, independently, hydrogen or non-hydrogen substituents comprising alkyls, alkenyls, oxa-alkyls, aralkyls and aryls; and X, $X_1$, Y and Z are, independently, oxygen, amine or sulfur, with preferred compounds being those in which X, $X_1$, Y and Z are oxygen, and $R_1$, $R_2$, $R_3$, $R_5$, $R_6$, $R_7$, $R_8$, $R_9$, $R_{10}$ and $R_{11}$ are hydrogen.

28 Claims, No Drawings

OXA ACIDS AND RELATED COMPOUNDS FOR TREATING SKIN CONDITIONS

This is a division, of application Ser. No. 08/658,089 filed Jun. 4, 1996 now U.S. Pat. No. 5,847,003.

FIELD OF INVENTION

The present invention relates to a new class of compounds for use as active principals for topical treatment of skin conditions, to compositions containing these compounds and to methods of treating skin conditions using these compounds and compositions. Compounds of the class include those of Formula (X):

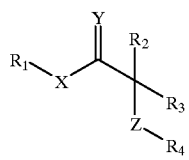

(I)

where $R_4$ is $(CR_5R_6-CR_7R_8-X_1)_n-CR_9R_{10}R_{11}$; n is an integer from 1 to 18; $R_1$, $R_2$, $R_3$, $R_5$, $R_6$, $R_7$, $R_8$, $R_9$, $R_{10}$, and $R_{11}$ are, independently, hydrogen or non-hydrogen substituents comprising alkyls, alkenyls, oxa-alkyls, aralkyls and aryls; and X, $X_1$, Y and Z are, independently, oxygen, amine, or sulfur, with preferred compounds being those in which X, $X_1$, Y and Z are oxygen, and $R_1$, $R_2$, $R_3$, $R_5$, $R_6$, $R_7$, $R_8$, $R_9$, $R_{10}$ and $R_{11}$ are hydrogen.

BACKGROUND OF THE RELATED ART

Dermal use of all carbon backbone, alpha hydroxyacids is described in U.S. Pat. No. B1 5,091,171, and cosmetic compositions using 2-hydroxyalkenoic acid are known such as described in U.S. Pat. No. 5,108,751. Such compounds must have an unsubstituted alpha hydoxy group on their all carbon backbone, chemical structure, and are purportedly used for beneficial effects to skin. The trend, however, is away from such alpha hydroxyacids as their use necessitates low operational pH ranges which for the most common forms such as glycolic and lactic acids have been known to cause skin irritations.

Topical formulations comprised of straight, all carbon backbone, dicarboxylic acids have been proposed to replace the fashionable alpha hydroxyacids. For example, U.S. Pat. Nos. 4,292,326, 4,386,104 and 5,385,943 claim that dicarboxylic acids having 7 to 13 carbon atoms could be used for various skin indications. Similarly, U.S. Pat. No. 4,885,282 states that a 4 to 18 carbon dicarboxylic acid compound is useful for skin disorders.

The problem with use of these dicarboxylic acids is their inherent insolubility in aqueous solutions which make up the bulk of cosmetic delivery systems. Such all carbon backbone, dicarboxylic acids are solids at ambient temperatures, are extremely difficult to work with, and if a solution is ever achieved, the result is an aesthetically unpleasant mixture unsuitable for cosmetic use.

There is a need in the art for a class of compounds that can be used as mild, exfoliating actives for topical treatment of skin.

There is also a need in the art for a mild, exfoliating topical composition which contains a water soluble compound that is amenable for manufacturing aesthetically acceptable cosmetic or dermatologic products.

OBJECTS OF THE INVENTION

It is an object of the present invention to provide a topical composition with multiple skin care benefits.

Another object of the present invention is to provide a class of water soluble compounds that are amenable for manufacturing aesthetically acceptable, mild, exfoliating compositions for topical use.

A further object of the present invention is to provide a new, dermatologic and cosmetic use for oxa acids and related compounds. These and other objects will become evident from the disclosure provided below.

SUMMARY OF INVENTION

The active compounds used in the treatment methods and the compositions of this invention are compounds of Formula (I):

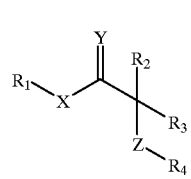

(I)

wherein, $R_4$ is $(CR_5R_6-CR_7R_8-X_1)_n-CR_9R_{10}R_{11}$; n is an integer from 1 to 18;

$R_1$, $R_2$, $R_3$, $R_5$, $R_6$, $R_7$, $R_8$, $R_9$, $R_{10}$ and $R_{11}$ are, independently, hydrogen or non-hydrogen substituents, with the non-hydrogen substituents including, but not limited to, alkyls, alkenyls, oxa-alkyls, aralkyls and aryls; and X, $X_1$, Y and Z are, independently, an oxygen (O), an amino group (NH) or a sulfur (S). Preferred compounds include those in which X, $X_1$, Y and Z are all oxygen, and $R_1$, $R_2$, $R_3$, $R_5$, $R_6$, $R_7$, $R_8$, $R_9$, $R_{10}$ and $R_{11}$, are all hydrogen.

Examples of non-hydrogen substituents include methyl, ethyl, propyl, isopropyl, butyl, isobutyl, hexyl, heptyl, octyl, nonyl, dodecanyl, methoxy, ethoxy, propoxy, butoxy, cyclohexenyl, hydroxymethyl, hydroxyethyl, hydroxypropyl, cyclobutyl and cyclohexanyl.

X, $X_1$, Y and Z are independently, O, NH, or S. Most preferred are those compounds in which X, $X_1$, Y and Z are each oxygen, and $R_1$, $R_2$, $R_3$, $R_5$, $R_6$, $R_7$, $R_8$, $R_9$, $R_{10}$ and $R_{11}$ are each hydrogen.

As defined herein, all compounds of the class identified by Formula (I) above will, collectively, be referred to as "oxa acids" and/or "oxa compounds" regardless of whether any or all of X, $X_1$, Y and Z are, independently, oxygens, sulfurs or amino groups.

The methods of treatment and the topical compositions of the present invention can further comprise mixtures of two or more compounds of Formula (I).

The present invention provides topical compositions comprising compounds of Formula (I), methods of treating skin conditions using compounds of Formula (I), and methods of treating skin conditions using compositions comprising compounds of Formula (I) and a suitable topical vehicle.

DETAILED DESCRIPTION OF THE INVENTION

The present invention includes the surprising discovery that the class of compounds of Formula (I) can be used as active principals in topical applications to treat various skin conditions attributed to, accompanied by or exacerbated by abnormal desquamation including dry skin, ichthyosis, palmar and plantar hyperkeratoses, dandruff, lichen simplex chronicus, Dariers disease, keratoses, lentigines, age spots, melasmas, blemished skin, acne, psoriasis, eczema, pruritis, inflammatory dermatoses, striae distensae (i.e. stretch marks), warts and calluses.

The compounds are unexpectedly and surprisingly found to be useful as active agents in topical preparations for treating signs of dermatological aging, both photoaging and intrinsic aging, including skin wrinkles such as fine wrinkling in the eye area or "crows feet," or fine wrinkles around the mouth area, irregular pigmentation, sallowness, loss of skin resilience and elasticity.

The present compounds of Formula (I) and topical compositions containing them are also useful for treating disorders associated with the nails, cuticles and hair such as ingrown hair, folliculitis and Pseudofolliculitis barbae. It has been discovered that the present compounds soften hair and promote the elimination of hair ingrowths, and are particularly useful for shaving.

Exemplary compounds of Formula (I) for the methods of treatment and the topical compositions of the present invention include 3,6-dioxaheptanoic acid [$CH_3$—O—$CH_2$—$CH_2$—O—$CH_2$—COOH]; 7,7-dimethyl-3,6-dioxaheptanoic acid [$(CH_3)_2$CH—O—$CH_2$—$CH_2$—O—$CH_2$—COOH]; 3,6-dioxaheptanoic acid ethyl ester [$CH_3$—O—$CH_2$—$CH_2$—O—$CH_2$—$COOC_2H_5$]; 3,6-dioxaheptanoic acid amide [$CH_3$—O—$CH_2$—$CH_2$—O—$CH_2$—$CONH_2$]; 3,6-dioxaheptanoic acid dodecyl ester [$CH_3$—O—$CH_2$—$CH_2$—O—$CH_2$—$COOC_{12}H_{25}$]; 2-phenyl-3,6-dioxaheptanoic acid [$CH_3$—O—$CH_2$—$CH_2$—O—CH(Phe)—COOH]; 2-benzyl-3,6-dioxaheptanoic acid [$CH_3$—O—$CH_2$—$CH_2$—O—CH($CH_2$—Phe)—COOH]; 2-methyl-3,6-dioxaheptanoic acid [$CH_3$—O—$CH_2$—$CH_2$—O—CH($CH_3$)—COOH]; 3-amino-6-oxaheptanoic acid [$CH_3$—O—$CH_2$—$CH_2$—NH—$CH_2$—COOH]; 3,6,9-trioxadecanoic acid [$CH_3$—O—$CH_2$—$CH_2$—O—$CH_2$—$CH_2$—O—$CH_2$—COOH]; 2-phenyl-3,6,9-trioxadecanoic acid [$CH_3$—O—$CH_2$—$CH_2$—O—$CH_2$—$CH_2$—O—CH(Phe)—COOH]; 2-benzyl-3,6,9-trioxadecanoic acid [$CH_3$—O—$CH_2$—$CH_2$—O—$CH_2$—$CH_2$—O—CH($CH_2$—Phe)—COOH]; 2-decyl-3,6,9-trioxadecanoic acid [$CH_3$—O—$CH_2$—$CH_2$—O—$CH_2$—$CH_2$—O—CH($C_{10}H_{21}$)—COOH]; 3,6,9,12-tetraoxatridecanoic acid [$CH_3$—O—$CH_2$—$CH_2$—O—$CH_2$—$CH_2$—O—$CH_2$—$CH_2$—O—$CH_2$—COOH]; 3,6,9,12,15-pentaoxahexadecanoic acid [$CH_3$—O—$CH_2$—$CH_2$—O—$CH_2$—$CH_2$—O—$CH_2$—$CH_2$—O—$CH_2$—$CH_2$—O—$CH_2$—COOH]; 2-methyl-3,6,9-trioxadecanoic acid [$CH_3$—O—$CH_2$—$CH_2$—O—$CH_2$—$CH_2$—O—CH($CH_3$)—COOH]; 10,10-dimethyl-3,6,9-trioxadecanoic acid [$(CH_3)_2$CH—O—$CH_2$—$CH_2$—O—$CH_2$—$CH_2$—O—$CH_2$—COOH]; 2-ethyl-3,6,9,12-tetraoxatridecanoic acid [$CH_3$—O—$CH_2$—$CH_2$—O—$CH_2$—$CH_2$—O—$CH_2$—$CH_2$—O—CH($C_2H_5$)—COOH]; 10-phenyl-3,6,9-trioxadecanoic acid [Phe—$CH_2$—O—$CH_2$—$CH_2$—O—$CH_2$—$CH_2$—O—$CH_2$—COOH]; 3,6,9-trioxadecanoic acid ethyl ester [$CH_3$—O—$CH_2$—$CH_2$—O—$CH_2$—$CH_2$—O—$CH_2$—$COOC_2H_5$]; 3,6,9-triaminodecanoic acid [$CH_3$—NH—$CH_2$—$CH_2$—NH—$CH_2$—$CH_2$—NH—$CH_2$—COOH]; 3,6,9,12-tetraminotridecanoic acid [$CH_3$—NH—$CH_2$—$CH_2$—NH—$CH_2$—$CH_2$—NH—$CH_2$—$CH_2$—NH—$CH_2$—COOH]; 9-amino-3,6-dioxadecanoic acid [$CH_3$—NH—$CH_2$—$CH_2$—O—$CH_2$—$CH_2$—O—$CH_2$—COOH]; 6,9-diamino-3-oxadecanoic acid [$CH_3$—NH—$CH_2$—$CH_2$—NH—$CH_2$—$CH_2$—O—$CH_2$—COOH]; 3,6,9-trithiodecanoic acid [$CH_3$—S—$CH_2$—$CH_2$—S—$CH_2$—$CH_2$—S—$CH_2$—COOH]; 9,12-dithio-3,6-dioxatridecanoic acid [$CH_3$—S—$CH_2$—$CH_2$—S—$CH_2$—$CH_2$—O—$CH_2$—$CH_2$—O—$CH_2$—COOH]; 9-amino-3,6-dioxadecanoic acid monoamide [$CH_3$—NH—$CH_2$—$CH_2$—O—$CH_2$—$CH_2$—O—$CH_2$—$CONH_2$]; 3,6,9-trioxadecanoic acid monoamide [$CH_3$—O—$CH_2$—$CH_2$—O—$CH_2$—$CH_2$—O—$CH_2$—$CONH_2$]; 10,10-dimethyl-3,6,9-trioxadecanoic acid amide [$(CH_3)_2$CH—O—$CH_2$—$CH_2$—O—$CH_2$—$CH_2$—O—$CH_2$—$CONH_2$]; 10,10-dimethyl-3,6,9-trioxadecanoic acid ethyl ester [$(CH_3)_2$CH—O—$CH_2$—$CH_2$—O—$CH_2$—$CH_2$—O—$CH_2$—$COOC_2H_5$]; 10,10-dimethyl-3,6,9-trioxadecanoic acid heptadecanyl ester [$(CH_3)_2$CH—O—$CH_2$—$CH_2$—O—$CH_2$—$CH_2$—O—$CH_2$—$COOC_{17}H_{35}$]; and 10,10-dimethyl-3,6,9-trioxadecanoic acid [$(CH_3)_2$CH—O—$CH_2$—$CH_2$—O—$CH_2$—$CH_2$—O—CH($CH_3$)—COOH]. The methods and compositions of the present invention can also advantageously comprise two or more different compounds of Formula (I).

Compounds within this class are described as intermediates in making curing agents and hardeners for epoxy resins in U.S. Pat. Nos. 5,017,675 and 5,319,004, both assigned to Hoechst AG. German Published Application No. DE-A-2936123 describes the preparation of such epoxy resin intermediate compounds. Such compounds are also commercially available from Hoechst AG.

Other compounds in the class can also be prepared from commercially available polyamines, polyols and polythiols via routine chemical reactions well known to those skilled in the art such as amidations, catalytic oxidations, esterifications and other well known organic chemistry synthetic protocols such as described in organic chemistry textbooks including March, *Advanced Organic Chemistry: Reactions, Mechanisms, and Structure*, 3rd ed., John Wiley Interscience (1985) and Carey et al., *Advanced Organic Chemistry*, 3rd ed., Parts A and B, Plenum Press, New York (1990).

The oxa compounds can be incorporated into the compositions as free acids or as corresponding salts derived by neutralization with organic or inorganic bases such as triethanolamine, arginine, lysine, potassium hydroxide, sodium hydroxide, lithium hydroxide, ammonium hydroxide or their like. The pH of the oxa acid composition can also be adjusted by adding water soluble salts formed by strong bases (e.g. KOH, NaOH, $NH_4OH$) and weak acids (e.g. phosphoric acid, acetic acid, lactic acid, carbonic acid). Examples of such salts include potassium biphosphate, sodium phosphate, sodium acetate, sodium lactate and the like. Other methods of adjusting the pH of the topical compositions of the present invention are well known to those skilled in the art.

The oxa compounds used in the methods of treatment and the topical compositions of this invention can also be used in the form of derivatives that are converted back to the acidic form by action of hydrolytic enzymes in the skin such as glycosidases, phosphatases, esterases and amidases. Examples of suitable derivatives of oxa acids include their esters with aliphatic alcohols or with carbohydrates, amides, lactones and anhydrides.

As used herein, "topical application" means spreading or laying directly onto the surface of skin; a "topical composition" means a composition intended to be directly layed onto or spread on the surface of skin; an "effective amount" means an amount of a compound or a composition sufficient to induce a positive change (e.g. normalization of desquamation) in the skin condition to be treated such as those attributed to, accompanied or exacerbated by abnormal desquamation; and a "physiologically acceptable vehicle" or a "suitable topical vehicle" mean drugs, cosmetics, medicaments or inert ingredients which the terms describe that are suitable for use in direct contact with human tissues without undue toxicity.

The present invention includes methods by which these compounds can be used to address the aforementioned skin conditions. Such methods include topically applying an effective amount of one or more compounds of Formula (I) to the affected skin areas normally once or twice daily. Such methods also include topically applying a composition containing an effective amount of one or more compounds of Formula (I) in a physiologically acceptable vehicle to the affected skin areas, normally once or twice daily. The methods of the present invention include the topical application of the compounds of Formula (I) in concentrations of up to 100%, when such compounds are a liquid at ambient temperature (e.g. 3,6,9-trioxadecanoic acid), such as when using the oxa compounds for skin peels or for softening hair.

When used in combination with a physiologically acceptable vehicle to form a topical composition, the effective amount of the compounds of Formula (I) can be within the range from about 0.1% to about 95%. Both the effective amount and the frequency of application will vary depending on the particular skin condition treated, the age and physical condition of the person under treatment, the severity of the condition, the duration of treatment, the nature of concurrent treatments, the specific compound or compositions employed, the particular vehicle utilized to deliver the compound or compositions, and like factors within the knowledge and expertise of those skilled in the art.

It has also been discovered that the efficacy of these compounds in treating skin conditions can be affected by the pH of the composition. It is desirable to maintain the pH in the acid range pH<7.0, preferably pH<5.0, most preferably in the pH range between 3.5 and 4.0.

The compounds of Formula (I) used in the methods of treatment and topical compositions of this invention are structurally distinct from other known compounds which have been used for skin conditions such as alpha hydroxyacids and dicarboxylic acids. When compared to alpha hydroxyacid formulations, the present invention delivers a class of compounds which have clear advantages such as superior mildness for skin. Formulations with alpha hydroxyacids such as glycolic and lactic acids cause substantial discomfort in some individuals and symptoms of severe skin irritation in others, upon facial application.

While being significantly gentler to skin than the glycolic acid formulation, the-oxa acid compositions are highly effective in normalizing the desquamation of the upper stratum corneum which is the mode of activity that is prerequisite for alleviating the skin conditions listed hereinabove.

The advantages of oxa compounds over dicarboxylic acids include better water solubility and superior stratum corneum desquamatory activity. Oxa acids easily dissolve in water to concentrations of at least 20 to 30% by weight and, therefore, allow a much wider range of composition flexibility. Straight, all carbon backbone, dicarboxylic acids of moderate to long chain length are virtually insoluble in water or, for that matter, in any other aesthetically acceptable vehicle. This severely limits the choice of delivery vehicles for the dicarboxylic acids. Desquamatory activity of all carbon backbone dicarboxylic acids is also questionable. For example, it is known that formulations containing 5% and 10% dodecanedioic acid do not produce any normalizing effect on stratum corneum desquamation beyond that of its vehicle alone.

The oxa compounds of the present invention can be used alone or in combinations with other cosmetic and pharmaceutical actives and excipients. The oxa acids can be readily used in compositions containing other cosmetic and pharmaceutical agents such as antifungals, vitamins, sunscreens, retinoids, antiallergenic agents, depigmenting agents, antiinflammatory agents, anesthetics, surfactants, moisturizers, exfolients, emulsifiers, stabilizers, preservatives, antiseptics, emollients, thickeners, lubricants, humectants, chelating agents, fragrances, colorants and skin penetration enhancers. Use of the oxa compounds in combination with any one of several of the above classes of actives will provide additional dermatological and/or cosmetic benefits unattainable when the above actives are used without the oxa compounds of this invention.

The composition may also contain emulsifiers that can be cationic, anionic, non-ionic or amphoteric, or a combination thereof. Non-ionic emulsifiers are preferred. Exemplary nonionic emulsifiers are commercially available sorbitans, alkoxylated fatty alcohols and alkyl polyglycosides. Anionic emulsifiers may include soaps, alkyl sulfates, monoalkyl and dialkyl phosphates, alkyl sulphonates and acyl isethionates. Other suitable emulsifiers can be found in McCutcheon, *Deteroents and Emulsifiers*, North American Edition, pp. 317–324 (1986), the contents of which are incorporated herein by reference.

If the present compositions need preservation, suitable preservatives include alkanols, especially ethanol and benzyl alcohol, parabens, sorbates, diazolidinyl urea, and isothiazolinones.

Examples of thickening agents suitable for use with the present oxa acids include xanthan gum, xanthan gum brine tolerant, hydroxypropyl cellulose, hydroxyethyl cellulose, carbopol and gum acacia, Sepigel 305 (available from Seppic Co., France), vee-gum or magnesium aluminum silicate. The oxa acids are also compatible with and their utility can be enhanced by humectants, for example urea, PCA, amino acids, certain polyols and other compounds with hygroscopic properties.

The compounds of this invention can be combined with most conventional emollients such as mineral oil, petrolatum, paraffin, ceresin, ozokerite, microcrystraline wax, perhydrosqualene, dimethyl polysiloxanes, methylphenyl polysiloxanes, silicone-glycol copolymers, triglyceride esters, acetylated monoglycerides, ethoxylated glycerides, alkyl esters of fatty acids, fatty acids and alcohols, lanolin and lanolin derivatives, polyhydric alcohol esters, sterols, beeswax derivatives, polyhydric alcohols and polyethers, and amides of fatty acids. Other suitable emollients can be found in Sagarin, *Cosmetics, Science and Technology*, 2nd Ed., vol. 1, pp. 32–43 (1972), the contents of which are incorporated by reference herein.

Another beneficial use of oxa acids is in topical compositions alongside keratolytic agents such as salicylic acid and benzoyl peroxide, and skin lightening agents such as kojic acid, benzoquinone, licorice derivatives, ascorbic acid and its derivatives (e.g. magnesium ascorbyl phosphate), glycerhetinic acid and its derivatives. The oxa acids can also be used readily with organic and inorganic sunscreens such as titanium dioxide, zinc oxide, benzylidene camphor, anthranilates (e.g. methyl, menthyl, phenyl, benzyl, phenylethyl, linalyl, terpinyl, cyclohexenyl and cycloheptenyl esters, and o-amino-benzoates), saliaylates (amyl, phenyl, benzyl, menthyl, glyceryl, octyl, dipropyleneglycol ester and cholesteryl salicylate), cinnamic acid derivatives (menthyl, octyl, 2-ethylhexyl, benzyl, alphaphenyl cinnamonitrile, and butyl cinnamoyl pyruvate), dihydroxycinnasic acid derivates (umbelliferone, methylumbelliferone, methylacetoumbelliferone), trihydroxycinnamic acid derivatives (esculetin, methyl esculetin, daphnetin, and the glucosides, esculin and daphrun), naphtholsulphonates (salts of 2-napthol-3,6-disulfonic acid and of 2-naphthol-6,8-disulfonic acids), dihydroxynaphthoic acid and its salts, ortho- and para-hydroxybiphenyldisulfonates, safe coumarine derivatives, diazoles (e.g. 2-acetyl-3-benzothiazoles), quinoline derivatives (salts of 8-hydroxyquinoline, 2-phenylquionoline), quinine salts, uric and violuric acids, tannic acid and its derivatives, dioxybenzone, benzoresorcinol, 2,2', 4,4'-tetra-hydroxybenzophenone, etocrylene. Of these, the cinnamic acid derivatives are preferred.

The utility of the oxa acids can be further enhanced by their co-formulation with (i) retinoids such as, by way of example, retinol, retinoic acid, retinyl palmitate, retinyl propionate, retinyl acetate, isotretinoin as well as synthetic retinoid mimics; (ii) hormonal compounds such as, by-way of example, estriol, estradiol, estrone or conjugated estrogens; (iii) alpha-hydroxyacids or polyhydroxy alpha-hydroxy acids such as glycolic acid, lactic acid, tartaric acid, gulonic acid and other carboxylic acids and their monomeric, polymeric, cyclic or acyclic derivatives having a free or a substituted hydroxy-, thiol-, selenyl- or a non-basic amine group in the alpha-position relative to the carboxyl group; (iv) with alpha-keto acids, such as, by way of example, pyruvic acid, 2-oxapropanoic acid, 2-oxabutanoic acid, 2-oxapentanoic acid, and the like.

Oxa acids are also compatible with and can be utilized for additional benefits in topical forumulations alongside:

(i) vitamins, enzyme co-factors such as vitamin B6 (pyrodoxine-HCl), vitamin B12 (cyanocobalamin), vitamin $D_3$ (cholecalcipherol), 1,25-dihydroxy vitamin $D_3$, vitamin B1 (thiamine), vitamin B2 (riboflavin), vitamins $K_n$, vitamin E (tocopherol), tocopheryl acetate, tocopheryl hemisuccinate, tocopheryl ascorbyl phosphate, tocopheryl linoleate, tocotrienols and their derivatives, nicotinic acid and its esters, pantothenic acid and its esters, panthenol, folic acid and its derivatives, choline, carnitine and substances without formal vitamin status or "pseudo-vitamins" such as vitamin F or cis,cis-linoleic acid, vitamin M or pteroyl-glutamic acid, vitamins B10 and B11, vitamin T also known under such names as "sesame seed factor", termitin, penicin, insectine, hypomycin and mycoine, vitamin L or anthranilic acid, vitamin L2 or adenylthiomethylpentose, myoinositol or cis-1,2,3,5-trans-4-6-cyclohexanehexol and its esters, especially phytic acid, laetrile or 1-mandelo-nitrile-beta-glucuronic acid, amygdalin, vitamin B15 or pangamic acid, vitamin B13 or orotic acid, vitamin $H_3$ or procaine hydrochloride, vitamin U or methylsulfonium salts of methionine, and pyrroloqujonoline quinone;

(ii) effective amounts of antifungal agents such as clotrimazole, ketoconazole, miconazole, naftifine, tolnaftate, amphotericin B, nystatin, 5-fluorocytosine, griseofulvin, haloprogin, of which tolnaftate, halopro-gin and miconazole are most preferred;

(iii) self-tanning agents such as dihydroxyacetone and lawsone, of which the former one is most preferred;

(iv) anti-mycobacterial agents, such as erythromycin, tetracyclin and related compounds, especially doxycy-clin and methacyclin, cephalosporins, penicillins, phenazines, especially clofazimine, rifamycins, especially rifampin, sulfones, especially 4,4' diaminodiphenyl sulfone, pyrazineamide, thiosemicarbazones, especially benzaldehyde thiosemicarbazone, thioureas, especially 4,4-disubstituted diphenylthioureas, viomycin, macrolide, aminoglycoside and peptide compounds selected from the group consisting of novobiocin, vancomycin, oleandomycin, paromomycin, leucomycins, fortimycin, colistin, crycloserine, dactinomycin, bicyclomycin, amphomy-cin with macrolide molecules preferred over the polypeptide compounds, quinolone derivatives, especially nalidixic acid, oxolinic acid, norfloxacin, cipro-floxacin and flumequine, and other compounds which interfere with bacterial cell wall synthesis, membrane function, RNA metabolism, purine, pyrimidine and protein synthesis, respiration or phosphcrylation;

(v) topical analgesics, such as lidocaine, benzocaine, butamben, butacaine, dimethisoquin, diperodon, dyclonine, pramoxine, tetracaine, chlorobutanol, clove oil, eugenol, of which benzocaine and lidocaine are most preferred;

(vi) lipidic compounds essential for the skin's barrier function such as ceramides, essential fatty acids and their esters, especially glycerides, ω-hydroxy fatty acids and their esters derived with alkanols through carboxylic hydroxyl or with other fatty acids at the omega-hydroxyl, the latter type being most preferred, with phospholipids, cholesterol and its esters, such as cholesteryl hemisuccinate and cholesteryl phospate of which cholesterol phospate and essential fatty acids are most preferred, phytosterols, cholestanol and its derivatives. The lipidic compounds can be added to a topical composition either as singular molecular entities or as a complex mixture of lipids derived from either synthetic, animal or plant sources;

(vii) antiallergenic agents and H1 and/or H2 antihistamines such an diphenylhydramine, clemizole, antazoline, thenaldine, phenyltoloxamine citrate, doxyl amine and its salts, diphenylpyraline, medrylamine, clemastine, pheniramine and its halogenated derivatives and salts, especially pehniramine maleate, buclizine, triprolidine and its salts, phenothiazines and related analogs, especially fenethazine hydrochloride and parathiazine hydrochloride, dibenz[b,s]azepines, especially, trapane, other tricyclic antiallergenics such as ketotifene, dithiadene and 3-thienylsulfide of thiadene, H2-receptor blockers, especially burimamide, metiamide and cimetidien, cromolic acid and its salts, khellin, kiethylcarbamazine, piriprost;

(viii) topical anti-inflammatory agents that can reduce inflammation at a concentration from about 0.025% to 10%, preferably, 0.5–1%, with the concentration of the anti-inflammatory adjusted up or down depending upon the potency of the utilized agents. Examples of steroidal anti-inflammatories that can be used with oxa acids in practicing this invention include hydrocortisone, hydroxytriamcilone, alpha-methyl dexamethasone, dexamethasone phosphate, beclamethasone dipropionate, clobetasol valerate, desonide, desoxymethasone, desoxycorticosterone acetate, dexamethasone, dichlorisone, diflorasone diacetate, diflucortolone and its derivatives, fluadrenolone, flu-crolone acetonide, fluocinonide, flucortine butyl ester, fluocortolone, fluprednidine, acetate, flurandrenolone, halcinonide, hydrocortisone acetate, hydrocortisone butyrate, methylprednisolone, triamcinolone acetonide, medrysone, amcinafide, betamethasone and its esters, chloroprednisone, chloroprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednison, and mixtures thereof, with the most preferred being prednisolone and hydrocortisone; and (ix) non-steroidal anti-inflammatories can also be employed such as described in Rainsford, *Antiinflammatory and Anti-Rheumatic Drugs*, Vols. I–III, CRC Press, Boca Raton, Fla. (1985), and specific examples of suitable NSAID's include enolic acids, oxicams (e.g. piroxicam, isoxicam), fenamic acid derivatives, meclofenamic acid derivatives (e.g. sodium meclofenamate), flufenamic acid derivatives such as N-($\alpha,\alpha,\alpha$-trifluoro-m-tolyl) anthranilic acid), mefenamic acid derivatives (e.g. N-(2,3-xyl-yl) anthranilic acid), propionic acid esters such as ibuprofen, naproxen, benoxaprofen, flubiprofen, ketoprofen, suprofen, of which ibuprofen is most preferred, pyrazolidinediones such as feprazone, trimethasone, oxyphenbutazone, sulfinpyrazone, phenylbutazone, of which phenylbutazone is most preferred, the acetic acid-derivatives, such as diclofenac, fenclofenac, indomethacin, sulindac, tolmetin, isozepac, furofenac, clidanac, zomepirac, acematricin, of which indomethacin is most preferred, salicylic acid derivatives, such as asprin, safaprin, disalacid, benorylate, trisilate, of which aspirin and disalacid are most preferred.

The compositions of the invention may also include safe anti-inflammatory products of natural origin shown to possess anti-inflammatory activity such as aloe vera extracts, extracts from genus Rubis (Rubia Cordifolia), extracts from genus Commiphom (Commiphora Mukul), willow bark, matricarria flowers, arnica flower, comfrey root, fenugreek seed and the like known to those skilled in the art.

The composition of the invention can also contain antioxidants with phenolic hydroxy functions such as gallic acid derivataives (e.g. propyl gallate), bio-flavonoids (e.g. quercetin, rutin, daidzein, genistein), ferrulic acid derivatives (e.g. ethyl ferrulate, sodium ferrulate), 6-hydroxy-2,5,7,tetramethylchroman-2-carboxylic acid. The compositions may also contain effective concentrations of water soluble antioxidants such as, by way of example, uric acid, reductic acid, tannic acid, rosmarinic acid and catechins. Also of benefit is a coformulation of oxa acids with nitric oxide synthase inhibitors as a way of reducing skin redness, vasodilation and inflammatory reactions, especially in response to electromagnetic and ionizing radiation or to the action of chemically or biochemically aggresive compounds. The nitric oxide synthase inhibitors can be added at concentrations from about 0.05% to 10%, most preferably from 1% to 3%, and selected from the group consisting of guanidine derivatives, especially monoaminoguianidine and methylguanidine, L-arginine derivatives, especially $N^G$-nitro-L-arginine and its esters, $N^G$-monomethyl-L-arginine, 2-iminopipperidines and other 2-iminoazaheterocycles.

The inventive composition may also include about 0.025% to 5% with 0.5%–2% preferred and with 0.5–1% most preferred, of those compounds that are known to be electron spin-traps such as nitrones, N-tert-butylnitrone and $\alpha$-[4-pyridyl 1-oxide]-N-tertbutyl nitrone or other compounds known to form free radicals with half-life time of more than 1 min.

Other possible antioxidants that the composition may contain are those which have one or more thiol functions (—SH) in either reduced or non-reduced form such as glutathione, lipoic acid, thioglycolic acid, thiolactic acid, thioglycerol and cysteine. The levels of sulfhydryl antioxidants should not exceed 0.5% for cosmetic uses of the composition but may be higher for pharmaceutical uses as dictated by the considerations of efficacy. The composition may also include inorganic antioxidants such as sulfites, bisulfites, metabisulfite or other inorganic salts and acids containing sulfur in oxidation state +4. The preferred level of inorganic sulfur-containing antioxidants is about 0.01–0.5% with the most preferred level between about 0.1% and 0.4% by weight.

The oxa acids can also be used in compositions that contain insect repellents such as aliphatic, cyclic or aromatic amides, citronella oil, terpineol, cineole, neem oil and terephthalic acid and its esters. Other suitable insect repellents can be found in Technical Bulletin No. 1549 from the U.S. Department of Agriculture or in their Agricultural Handbook Nos. 69, 340 and 461.

The oxa acids are suitable for topical compositions that contain skin cooling compounds such as, by way of example, menthol, menthyl glycerol, assymetical carbonates, thiocarbonates and urethanes, N-substituted carboxamides, ureas or phosphine oxides such as described in *J. Cosmet. Chem.*, vol. 29, p. 185 (1978), menthyl lactate, and menthone glycerine acetal.

The compositions of the present invention can be made an lotions. A basic lotion would contain an effective amount of an oxa acid, up to 95% of water, up to 20% of an emollient and up to 10% of an emulsifier. Such lotions may be preserved with up to 5% of a preservative and contain up to 2–3% of a fragrance, and up to 5% of a dye or a pigment. The composition of the invention can also be formulated as a cream. A basic cream would normally include an effective amount of an oxa acid, up to about. 30% of an emollient, up to about 90% of water and up to about 20% of an emulsifier.

While such lotions or creams can be made via conventional homogenization methods known to those skilled in the art, it is also possible to make such lotions and creams via a process of microfluidization which involves co-mixing the aqueous phase and the oil phase of such creams and lotions in a high-pressure homogenizer which reduces the emulsion particle size dramatically to about $\frac{1}{400}$th the size of those in creams and lotions prepared without applying high pressure. Microfluidization allows one to prepare elegant stable creams and lotions containing effective amounts of an oxa acid without the use of traditional emulsifiers and surfactants.

The oxa acids cab also be formulated in the form of micro-emulsions. A micro-emulsion system would typically contain an effective amount of oxa acid, up to 18% of a hydrocarbon; up to 40% of an oil; up to 25% of a fatty alcohol; up to 30% of an nonionic surfactant; and up to 30% of water.

The oxa acids are suitable and convenient for use in topical products formulated in the form of oil-in-water or water-in-oil emulsion, gels, lotions, ointments, sticks, sprays, tapes, patches, as multiphase emulsion compositions, such as water-in-oil-in-water type as disclosed in U.S. Pat. No. 4,254,105, incorporated herein by reference. The compositions of the invention can also be formulated as triple emulsions of the oil-in-water-silicone fluid type as disclosed in U.S. Pat. No. 4,960,764 incorporated herein by reference.

The compositions of the invention can also be made as a liposomal formulation, for example, according to the methods described in Mezei, *J. Pharmaceut. Pharmacol.*, vol. 34, pp. 473–474 (1982) or modification thereof. In such compositions, droplets of the oxa acid solution can be entrapped inside the liposomal vesicles and then incorporated into the final formula with the shell of the liposome being a phospholipid but which can be replaced with other suitable lipids (e.g. skin lipids). The liposomes can then be added to any of the carrier systems described above according, for example, to the preparation modes, uses and compositions of topical liposomes as described in Mezei, *Topics in Pharmaceutical Sciences*, Breimer et al. Eds., pp. 345–358, Elsevier Science Publishers BV, New York (1985), incorporated herein by reference, or according to the reverse-phase evaporation method described in Szoka et al., *Proc. Nat. Acad. Sciences*, vol. 75, pp. 4194–4198 (1978), and also in Diploses et al., *J. Soc. Cosmetic Chemists*, vol. 43, pp. 93–100 (1992), all incorporated herein by reference.

Solutions of oxa acids can also be entrapped in polymeric vesicles with a shell consisting of a suitable polymeric material such as gelatin, cross-linked gelatin, polyamide, poylacrylates and the like. These vesicles can then be incorporated into any composition according to the disclosures herein.

The general activity and mildness to skin of the present oxa acids in a topical composition can also be enhanced by neutralization to pH 3.5 to 8.0, most preferably from pH 3.7 to 5.6, with one or more amphoteric and pseudoamphoteric compounds selected from a list containing, but not limited to, glycine, alanine, valine, serine, theronine, methionine, leucine, asparagine, histidine, glutamic acid, glutamine, lysine, cystine, cystein, tryptophan, serine, phenylalariine, citrulline, creatine, proline, 3- or 4-hydroxyproline, 5-hydroxylysine, ornithine and its derivatives, 3-aminopropanoic acid and other aminocarboxylic acids, canavanine, canaline, homoarginine, betaine, taurine, aminoaldonic acids and aminosugars, aminouronic acid, aminoaldaric acid, deacetylated hyaluronic acid, hyalobiuronic acid, chondrosine, desulfated heparin, neuraminic or sialic acid, thyroxine, di-iodotyrosine, methionine sulfone, glycylglycine, deacetylated chondroitin, DL-sphinngosine, sphingomyelin, L-(erythro)-sphingosine, ophidine, glucagon, homocarnosine, aminopipecolic acid, phosphytidyl serine, cocoamphoglycine, phospha-tidyl ethanolamine, cysteinesulfinic acid, glutathione, aluminum oxide, zinc oxide or other amphoteric inorganic oxides, polyamidoamines, polyamidoamines-based dendrimers, sodium hydroxymethyl-glycinate and polyethylene amine.

The utility and mildness of the present oxa acids in a topical composition can also be enhanced by certain chelating agents incorporated into the composition at levels from about 0.01% to about 25% by weight, more preferably from about 0.5% to 10%, and most preferably from about 1% to about 5%. Suitable examples of chelating agents include those that have a high affinity for zinc, calcium, magnesium, iron and/or copper ions, such as ethylene-diamine-tetra-acetic acid, (ethylenedioxy)-di-ethylene-dinitrilo-tetra-acetic acid, salicylaldoxime, quinolinol, diaminocyclohexane-tetra-acetic acid, diethylene-triamino-penta-acetic acid, dimethylglyoxime, benzoin oxime, triethylene-tetramine, desferrioxamine or mixtures thereof.

The following examples are illustrative of the present invention and are not intended to limit the invention thereby.

EXAMPLES

The compositions of the present invention are generally made into lotions, creams or gels for topical application.

Example 1

Preparation of Oxa Acid Topical Compositions

In a suitable vessel, water, glycerin, propylene glycol Na$_2$EDTA and 3,6,9-trioxadecanoic acid are added and mixed together. Ammionium hydroxide is added to the vessel in increments to adjust pH to the desired range. This pH-adjusted phase is then heated to 170–175° F. Hydroxyethyl cellulose is next added with agitation until uniform to complete phase A.

For the lotion and cream, phase B is added to a suitable, second vessel, combined and heated to 170–175° F. Phase B is then added to phase A with sufficient mixing, again at 170–175° F. The batch is then cooled to 120° F. Phase C is added to the batch and mixed until uniform. The chart below tabulates weight percentages of ingredients for exemplary gel, lotion and cream embodiments.

| Phase | | GEL | LOTION | CREAM |
|---|---|---|---|---|
| (A) | water | Q.S. | Q.S. | Q.S. |
| | glycerin | 5.00 | 3.00 | 5.00 |
| | propylene glycol | 3.00 | 3.00 | 3.00 |
| | disodium-EDTA | 0.10 | 0.10 | 0.10 |
| | 3,6,9-trioxa-decanoic acid | 10.00 | 10.00 | 10.00 |
| | hydroxyethyl cellulose | 0.50 | 0.30 | 0.50 |
| | ammonium hydroxide (30%) | to pH 3.7–3.9 | to pH 3.7–3.9 | to pH 3.7–3.9 |
| (B) | octyl palmitate | — | 3.00 | 5.00 |
| | myristyl myristate | — | 3.00 | 5.00 |
| | glyceryl monostearate | — | 1.50 | 3.00 |
| | cetearyl alcohol & Ceteareth-20 | — | 3.00 | 5.00 |
| | methyl paraben | — | 0.20 | 0.20 |
| (C) | imidazolidilyl urea | 0.30 | 0.30 | 0.30 |

All numbers are expressed as percentages of total weight of composition except for pH ranges and Q.S. for balance with water.

Those skilled in the art will readily perceive possible vehicles other than lotions, creams or gels, after having the benefit of this disclosure.

Microscopic normalization of desquamation of the stratum corneum or macroscopic exfoliation of the epidermis are the modes of activity that are prerequisite for alleviating the skin conditions for which the present oxa acid compounds and compositions are intended. The following example demonstrates, inter alia, the superior stratum corneum desquamatory activity provided by the present oxa acid compositions.

Example 2

Cream for Hynerpiamented Spots

This example illustrates a cream which can be prepared and used to reduce appearance of hyper-pigmentation spots on the skin of hands.

| | w/w % |
|---|---|
| isopropyl myristate | 3.0 |
| polyethylene glycol (1000) monostearate | 5.0 |
| palmitic acid | 10.0 |
| 3,6,9-trioxadecanoic acid | 10.0 |
| glycerine | 3.0 |
| polyethylene glycol (300) monostearate | 5.0 |
| methyl paraben | 0.2 |
| magnesium ascorbyl phosphate | 2.0 |

| | w/w % |
|---|---|
| water | 60.0 |
| perfume & color | to 100.0 |
| triethanolamine | to pH 4.0 |

All numbers are expressed as percentages of total weight of composition except for the reference to pH.

Example 3

Cream for Dry Skin, Ichthyosis and Hyperkeratoses

This example illustrates a silicone cream that can be prepared and used to treat dry skin, ichthyosis and hyperkeratoses according to the present invention.

| | w/w % |
|---|---|
| Phase A | 2.0 |
| laurylmethicone copolyol | 2.0 |
| mineral oil | 1.0 |
| lanolin | 1.5 |
| sunflower or soybean oil | 10.0 |
| cyclomethicone | 6.0 |
| oil soluble rosmary extract | 2.0 |
| Phase B | |
| sodium iodide | 2.0 |
| 3,6,9-trioxadecanoic acid | 9.0 |
| 3-amino-6-oxaheptanoic acid | 1.0 |
| sodium hydroxymethyl glycinate | 0.5 |
| demineralized water | to 100.0 |
| sodium biphosphate | to pH 3.8 |

All numbers are expressed as percentages of total weight of composition except for the reference to pH.

Example 4

Silicone Gel

This example illustrates a water-in-silicone gel composition.

| | w/w % |
|---|---|
| Phase A | |
| dimethiconol | 10.0 |
| dimethicone copolyol | 10.0 |
| cyclomethicone | 5.0 |
| Phase B | |
| 3,6-dioxaheptanoic acid | 8.0 |
| glycerine | 20.0 |
| demineralized water | to 100.0 |
| triethanolamine | to pH 4.0 |

All numbers are expressed as percentages of total weight of composition except for the reference to pH.

Example 5

Cream for Acne, Skin Blemishes and Age Spots

This example illustrates a face cream than can be used to treat acne, skin blemished and age spots.

| | w/w % |
|---|---|
| Phase A | |
| oleic acid | 1.0 |
| stearic acid | 17.0 |
| Polyoxyethylene (20 propylene glycol monostrearate | 10.0 |
| retinol | 0.1 |
| Phase B | |
| glycerine | 5.0 |
| 2-pyrollidone-5-carboxylic acid | 5.0 |
| 3,6,9-trioxadecanoic acid | 7.5 |
| 3,6-dioxaheptanoic acid amide | 2.5 |
| lactic acid | 3.0 |
| demineralized water | to 100.0 |
| ammonium hydroxide | to pH 4.2 |

All numbers are expressed as percentages of total weight of composition except for the reference to pH.

Various modifications and alterations to the present invention may be appreciated based on a review of this disclosure. These changes and additions are intended to be within the scope and spirit of this invention as defined by the following claims.

What is claimed is:

1. A topical composition comprising a suitable topical vehicle and a compound of Formula (I):

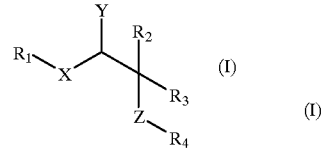

wherein $R_4$ is $(CR_5R_6\text{—}CR_7R_8\text{—}X_1)n\text{—}CR_9R_{10}R_{11}$; n is an integer from 1 to 18; $R_1$, $R_2$, $R_3$, $R_5$, $R_6$, $R_7$, $R_8$, $R_9$, $R_{10}$ and $R_{11}$ are, independently, hydrogen or substituents selected from the group consisting of alkyls, alkenyls, oxa-alkyls, aralkyls, aryls, cycloalkyls and cycloalkenyls; and X, $X_1$, Y and Z, are, independently, O or S, with the proviso that at least one of X, $X_1$, Y or Z is sulfur.

2. The composition of claim 1 wherein said compound of Formula (I) comprises about 0.1 to about 95 wt % of said composition, and wherein n in said compound is an integer from 2 to 12.

3. The composition of claim 1 further comprising a mixture of two or more different compounds of Formula (I).

4. The composition of claim 1, wherein said subtituents are selected from the group consisting of methyl, ethyl, propyl, isopropyl, butyl, isobutyl, hexyl, heptyl, octyl, nonyl, dodecanyl, methoxy, ethoxy, propoxy, butoxy, cyclohexenyl, hydroxymethyl, hydroxyethyl, hydroxypropyl, cyclobutyl and cyclohexyl.

5. The composition of claim 1 wherein $R_1$, $R_2$, $R_3$, $R_5$, $R_6$, $R_7$, $R_8$, $R_9$, $R_{10}$ and $R_{11}$ of said compound are each hydrogen.

6. The composition of claim 1 wherein X, $X_1$, Y and Z of said compound are each sulfur.

7. The composition of claim 1, wherein said compound is selected from the group consisting of 3,6,9-trithiodecanoic acid; 9,12-dithio-3,6-dioxatridecanoic acid; and a mixture thereof.

8. The composition of claim 1 further comprising at least one active selected from the group consisting of antifungals, vitamins, sunscreens, retinoids, antiallergenic agents, depigmenting agents, anti-inflammatory agents, anesthetics, surfactants, moisturizers, exfolients, emulsifiers, stabilizers, preservatives, antiseptics, emollients, thickeners, lubricants, humectants, chelating agents, fragrances, colorants, skin penetration enhancers, self-tanning agents, anti-mycobacterial agents, topical analgesics, lipidic compounds, H1 and/or $H_2$ antihistamines, natural extracts, antioxidants, bio-flavonoids, skin cooling compounds, insect repellents, and mixtures thereof.

9. The composition of claim 8, wherein the bio-flavonoid is selected from the group consisting of quercetin, rutin, daidzein, genistein, ferrulic acid derivatives, ethyl ferrulate, sodium ferrulate, 6-hydroxy-2,5,7,tetramethylchroman-2-carboxylic acid, and mixtures thereof.

10. The composition of claim 8, wherein the antioxidant is selected from the group consisting of gallic acid derivatives, uric acid, reductic acid, tannic acid, rosmarinic acid, catechins, and mixtures thereof.

11. The composition of claim 8, wherein the natural extract is selected from the group consisting of rosemary extract, sunflower oil, soybean oil, aloe vera extract, an extract from genus Rubis, an extract from genus Commiphom, willow bark extract, matricarria flower extract, arnica flower extract, comfrey root extract, fenugreek seed extract, and mixtures thereof.

12. The composition of claim 1, wherein said composition comprises up to about 60 wt % of said compound of Formula (I) and has a pH of less than 7.0.

13. The composition of claim 12, wherein said topical vehicle comprises up to about 95 wt % of water; up to about 30 wt % of an emollient; and up to about 20 wt % of an emulsifier.

14. The composition of claim 1, wherein said topical vehicle is selected from the group consisting of gels, lotions and creams.

15. The composition of claim 14, wherein said topical vehicle is comprised of an ingredient selected from the group consisting of ammonium hydroxide, cetearyl alcohol/Ceteareth-20, EDTA, glycerin, glyceryl monostearate, hydroxyethyl cellulose, imidazolidilyl urea, methyl paraben, myristyl myristate, octyl palmitate, propylene glycol, and mixtures thereof.

16. A method for treating skin conditions caused by, accompanied with or exacerbated by abnormal desquamation, comprising applying to said skin an effective amount of a compounds compound of Formula (I):

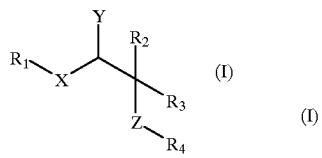

wherein $R_4$ is $(CR_5R_6—CR_7R_8—X_1)_n—CR_9R_{10}R_{11}$; n is an integer from 1 to 18; $R_1$, $R_2$, $R_3$, $R_5$, $R_6$, $R_7$, $R_8$, $R_9$, $R_{10}$ and $R_{11}$ are, independently, hydrogen or substituents selected from the group consisting of alkyls, alkenyls, oxa-alkyls, aralkyls, aryls, cycloalkyls and cycloalkenyls; and X, $X_1$, Y and Z, are, independently, O or S, with the proviso that at least one of X, $X_1$, Y or Z is sulfur.

17. The method of claim 16 wherein said compound is combined with a suitable topical vehicle in a topical composition.

18. The method of claim 17 wherein said compound of Formula (I) comprises about 0.1 to about 95 wt % of said composition, and wherein n in said compound is an integer from 2 to 12.

19. The method of claim 16 further comprising, applying to said skin an effective amount of a mixture of two or more different compounds of Formula (I).

20. The method of claim 16, wherein said substituents of said compound are selected from the group consisting of methyl, ethyl, propyl, isopropyl, butyl, isobutyl, hexyl, heptyl, octyl, nonyl, dodecanyl, methoxy, ethoxy, propoxy, butoxy, cyclohexenyl, hydroxymethyl, hydroxyethyl, hydroxypropyl, cyclobutyl and cyclohexyl.

21. The method of claim 16 wherein $R_1$, $R_2$, $R_3$, $R_5$, $R_6$, $R_7$, $R_8$, $R_9$, $R_{10}$, and $R_{11}$ of said compound are each hydrogen.

22. The method of claim 16 wherein X, $X_1$, Y and Z of said compound are each sulfur.

23. The method of claim 16, wherein said compound is selected from the group consisting of 3,6,9-trithiodecanoic acid; 9,12-dithio-3,6-dioxatridecanoic acid; and a mixture thereof.

24. The method of claim 16, further comprising at least one active selected from the group consisting of antifungals, vitamins, sunscreens, retinoids, antiallergenic agents, depigmenting agents, anti-inflammatory agents, anesthetics, surfactants, moisturizers, exfolients, emulsifiers, stabilizers, preservatives, antiseptics, emollients, thickeners, lubricants, humectants, chelating agents, fragrances, colorants, skin penetration enhancers, self-tanning agents, anti-mycobacterial agents, topical analgesics, lipidic compounds, H1 and/or H2 antihistamines, natural extracts, antioxidants, bio-flavonoids, skin cooling compounds, insect repellents, and mixtures thereof.

25. The method of claim 24, wherein the bio-flavonoid is selected from the group consisting of quercetin, rutin, daidzein, genistein, ferrulic acid derivatives ethyl ferrulate, sodium ferrulate, 6-hydroxy-2,5,7,tetramethylchroman-2-carboxylic acid, and mixtures thereof.

26. The method of claim 24, wherein the antioxidant is selected from the group consisting of gallic acid derivatives, uric acid, reductic acid, tannic acid, rosmarinic acid, catechins, and mixtures thereof.

27. The method of claim 24, wherein the natural extract is selected from the group consisting of rosmary extract, sunflower oil, soybean oil, aloe vera extract, an extract from genus Rubis, an extract from genus Commiphom, willow bark extract, matricarria flower extract, arnica flower extract, comfrey root extract, fenugreek seed extract, and mixtures thereof.

28. The method of claim 16, wherein said skin conditions to be treated are selected from the group consisting of dry skin, ichthyosis, palmar and plantar hyperkeratoses, dandruff, lichen simplex chronicus, Dariers disease, keratoses, lentigines, age spots, melasmas, blemished skin, acne, psoriasis, eczema, pruritis, inflammatory dermatoses, striae distensae, warts, calluses, signs of dermatological aging, skin wrinkles, fine wrinkles around the mouth area, irregular pigmentation, sallowness, loss of skin resilience and elasticity, disorders associated with nails, cuticles and hair such as ingrown hair, folliculitis and Pseudo-folliculitis barbae.

* * * * *

UNITED STATES PATENT AND TRADEMARK OFFICE
CERTIFICATE OF CORRECTION

PATENT NO. : 6,071,962
DATED : June 6, 2000
INVENTOR(S) : Dmitri Ptchelintsev, et. al.

It is certified that error appears in the above-identified patent and that said Letters Patent is hereby corrected as shown below:

In claim 1, please delete the structural formula

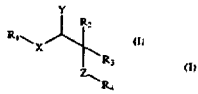

and insert the structural formula

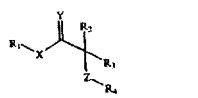

In claim 16, please delete the structural formula

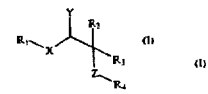

and insert the structural formula

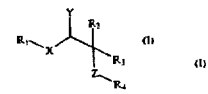

Further in claim 16, please delete the term -compounds- at line 4.

Signed and Sealed this

Twenty-second Day of May, 2001

Attest:

NICHOLAS P. GODICI

Attesting Officer

Acting Director of the United States Patent and Trademark Office